United States Patent [19]

Van Zile et al.

[11] Patent Number: 5,019,103
[45] Date of Patent: May 28, 1991

[54] TIBIAL WEDGE SYSTEM

[75] Inventors: Richard R. Van Zile; Donald E. McNulty, both of Warsaw, Ind.

[73] Assignee: Boehringer Mannheim Corporation, Indianapolis, Ind.

[21] Appl. No.: 475,176

[22] Filed: Feb. 5, 1990

[51] Int. Cl.$^5$ ............................................. A61F 2/38
[52] U.S. Cl. ...................................................... 623/20
[58] Field of Search .............................. 623/16, 18, 20

[56] References Cited

U.S. PATENT DOCUMENTS

| | | | |
|---|---|---|---|
| 4,479,271 | 10/1984 | Bolesky et al. | 623/20 |
| 4,834,081 | 5/1989 | Van Zile . | |
| 4,944,757 | 7/1990 | Martinez et al. | 623/20 |

OTHER PUBLICATIONS

Brochure entitled "Insall/Burstein ® II Modular Knee System", copyright 1989 by Zimmer, Inc. 21 pages.

*Primary Examiner*—David J. Isabella
*Attorney, Agent, or Firm*—Perman & Green

[57] ABSTRACT

A modular prosthetic system for mounting a variety of styles of wedges to a tibial tray in order to correct for bone deficiencies, alternatively, in the anterior/posterior direction and in the medial/lateral direction. The wedge is mounted on the tibial tray before the system is implanted. The tibial tray has a pair of spaced transverse smooth bores and coaxial counterbores and the wedge has a pair of spaced transverse threaded bores which are aligned, respectively, with the smooth bores and counterbores when the wedge is mounted on the tibial tray. Cannulated screws having a head, threaded shank, and longitudinal bore are attached so as to extend through an associated bore and counterbore, then are threadedly engaged with the wedge. A bone screw is then received through the bore of the cannulated screw for implanting the system on the proximal end of the tibia. Mating spherical surfaces, respectively, on the cannulated screw and on the bone screw enable the bone screw to attain an optimal orientation. In the event the system is to be implanted solely with cement rather than with screws, plugs are used to seal the bores in the cannulated screws.

12 Claims, 2 Drawing Sheets

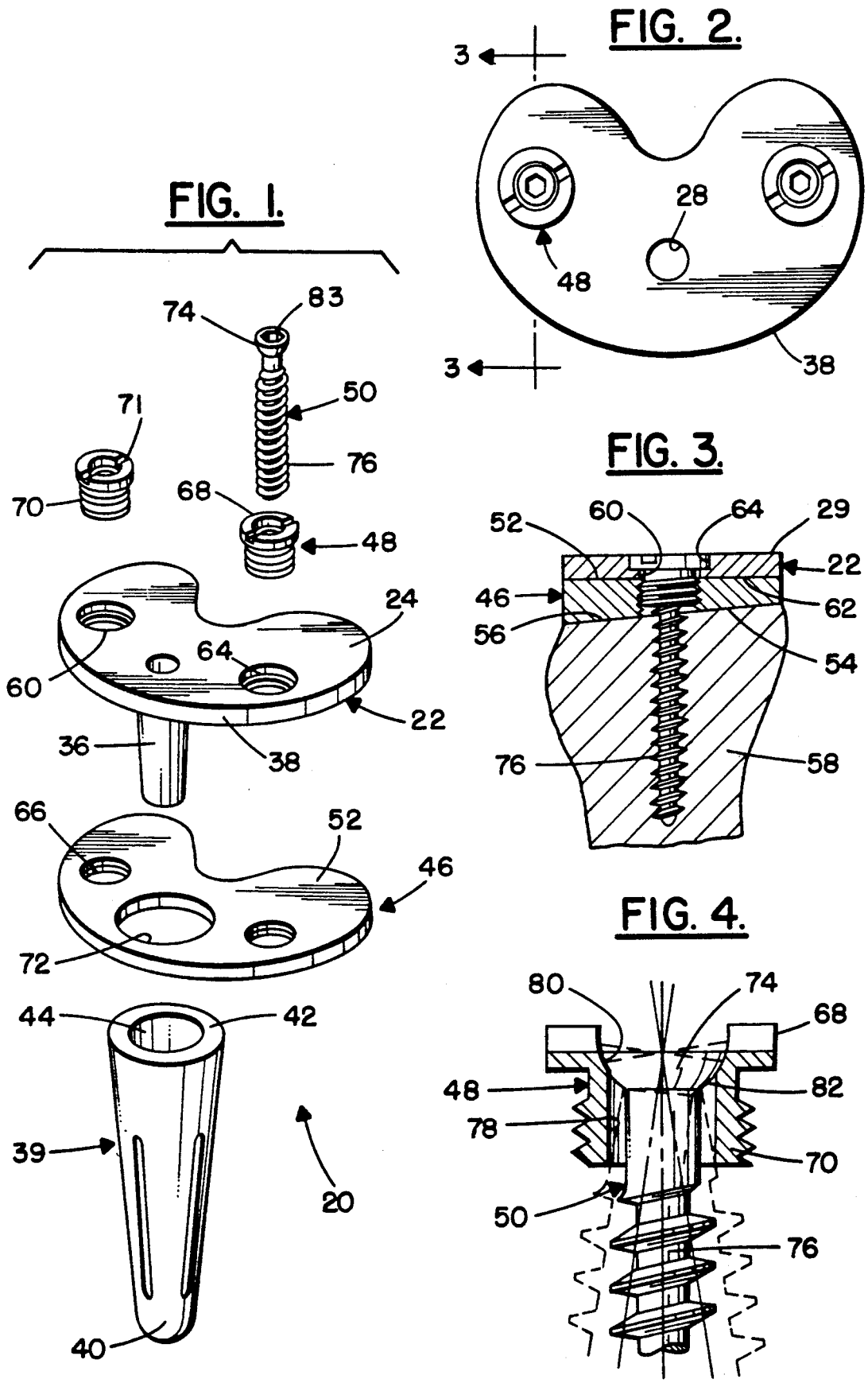

TIBIAL WEDGE SYSTEM

BACKGROUND OF THE INVENTION

1. Field of the Invention

The present invention relates generally to prosthetic joints and, more particularly, to a modular prosthetic knee joint construction which provides tibial wedges to compensate for a broad range of types and sizes of medial/lateral and anterior/posterior bone deficiencies.

2. Description of the Prior Art

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles.

When the knee joint is injured whether as a result of an accident or illness, cartilage covering the natural bones may become damaged to the extent that they are unable to function (articulate) properly. If the bones are affected beyond the level or degree where natural healing and new growth will remedy the damage, then a prosthetic replacement of the damaged portion is called for in order to relieve pain and to restore normal use to the joint. Typically the entire joint is replaced by means of a surgical procedure which involves removal of the ends of the corresponding damaged bones and replacement of these ends with prosthetic implants. A typical such implant would be for the hip joint wherein a metal implant could be anchored in the intramedullary canal of the femur and would provide a generally spherical protuberance extending outwardly therefrom. The mating prosthetic portion would be a polyethylene socket member suitably anchored into the acetabulum. While prosthetic devices of this type, normally including a physiologically inert metal member and an engaging high density polyethylene member, are well known in the art, these types of devices are of a fixed and unchanging nature once they are inserted (implanted) into the patient and anchored there, whether by pinning or by acrylic bone cement or both.

Due in part to the fact that the size, shape and anatomy of virtually every patient is different, great care must be taken by the orthopedic surgeon in order to select properly sized and shaped prosthetic members for implanting. In order to achieve a suitable fit and size compatibility, an extensive number of a variety of each type of prosthetic implant must be available to the orthopedic surgeon from which he may choose. As a result, the cost of inventory as well as the logistics of ordering and storing a wide variety of prosthetic implants is cumbersome. Therefore, it would be an improvement to this present situation if prosthetic devices could be structured with removable portions such that there would be a reduction in inventory without a corresponding compromise as to the number and variety of different prosthetic combinations which can be created. In order to provide such an improvement, it is necessary that the prosthetic portions which are to be mixed and matched into a variety of combinations be suitably secured together so that the prosthetic member, which they in combination create, is not weaker nor more likely to fail than would be a similar prosthetic member constructed as a single integral piece.

A further concern involves the procedure when a prosthetic device becomes worn or damaged and a replacement must be made. While this is possible, it oftentimes involves elaborate surgery depending upon the particular portion of anatomy involved and the extent or nature of the damage to the prosthetic device. Furthermore, certain portions of the anatomy such as knee joints may be more susceptible to wear due to the surface area of articulation, the nature of the anatomy and the typical loads and forces which are encountered by this particular joint. Repair and/or replacement may also be desired when interfacing portions of the anatomy change and the contacting portion of the prosthesis needs to be revised as to its shape or size.

By structuring a prosthetic implant such that the portion most likely to wear or desired to be changed is quickly and easily replaceable from the remaining portion of the prosthetic implant, significant amounts of surgical time can be saved and the prosthesis can be more closely tailored to the patient's needs. Equally important is the fact that the portion of the prosthesis which is anchored into the patient, such as a tapered shaft inserted into the intramedullary canal of the tibia or of the femur, does not have to be surgically removed in order to make a replacement of a worn or damaged tibia articulation portion. Such a replaceable concept, in order to be effective, must securely hold the anchored portion and the replaceable portion together so as to act as an integral member regardless of the nature or complexity of the forces and loads acting thereon. With a design which achieves the requisite strength and durability, it is then possible to mix and match the replaceable portion with various anchored portions and vice versa such that, for example, an inventory of five relatively large and expensive replaceable portions and five relatively small and inexpensive anchoring portions for a tibial or femoral implant would be able to provide 25 different combinations of each to the orthopedic surgeon rather than having to inventory and stock 25 separate complete relatively large and expensive portions.

Often included among the components used in a prosthetic knee joint system is a wedge employed to correct for naturally occurring or disease-caused or injury-caused unevenness of the tibial bone. In one instance, there may be an anterior/posterior deficiency on the tibia; in another instance there may be a varus/valgus deficiency; or there may be one or the other but present only in one compartment of the knee joint, that is, in the lateral compartment or in the medial compartment. The wedge compensates for the deficiencies and assures that, following implantation, the patient will eventually be able to stand and walk erect.

Tibial and femoral primary or revision knee prostheses that are presently being marketed often times have a fixed central stem, located on the distal plane of the tibial tray, or component, and on the proximal portion of the femoral component's anterior/posterior box. This stem is used primarily for purposes of stabilization and strength, both during installation and after the joint has been rebuilt. It may be difficult to determine prior to surgery, even radiographically, the size of the stem to be used. As a result, it is often necessary to wait until the bone structure is personally viewed by the surgeon during the implant operation before selecting the proper size of the implant, including a wedge, if required.

While wedges are known and commonly used, their use in a modular system offering the surgeon a variety of other options is not generally known. One important feature sought by the surgeon is a choice of the mode of fixation. While some surgeons prefer to use cement exclusively, others use bone screws, and still others prefer a combination of the two.

Although numerous devices and systems are presently known which generally satisfy the goals for which they were intended, none offer the simplicity, economy, accuracy, and options to the surgeon which are achieved by the present invention.

SUMMARY OF THE INVENTION

To this end, the invention relates to a modular prosthetic system for mounting a variety of styles of wedges to a tibial tray in order to correct for bone deficiencies alternatively, in the anterior/posterior direction and in the medial/lateral direction. The wedge is mounted on the tibial tray before the system is implanted. The tibial tray has a pair of spaced transverse smooth bores and coaxial counterbores and the wedge has a pair of spaced transverse threaded bores which are aligned, respectively, with the smooth bores and counterbores when the wedge is mounted on the tibial tray. Cannulated screws having a head, threaded shank, and longitudinal bore are attached so as to extend through an associated bore and counterbore, then are threadedly engaged with the wedge. A bone screw is then received through the bore of the cannulated screw for implanting the system on the proximal end of the tibia. Mating spherical surfaces, respectively, on the cannulated screw and on the bone screw enable the bone screw to attain an optimal orientation. In the event the system is to be implanted solely with cement rather than with screws, plugs are used to seal the bores in the cannulated screws.

The invention is characterized by its structural simplicity, ease of implantation, modularity, and the accuracy which can be obtained when it is used. A particularly notable feature resides in the options which are provided to the surgeon by the invention. It provides the surgeon with the opportunity to choose, during the surgical procedure, a wedge having the appropriate wedge angle, a full wedge or a half wedge, as desired, and the choice of wedges sloped in the anterior/posterior directions and in the medial/lateral directions.

Other choices available to the surgeon by reason of the invention include the means of fixation. In the event cement is chosen as the fixation vehicle, holes in the wedges can be appropriately plugged in order to prevent the escape of the cement into undesired locations. In the event screws are desired, the construction of the components enables them to assume an orientation relative to the tibial tray and to the wedge which may be other than perpendicular, yet which assures the strongest possible connection.

The system of the invention also provides the surgeon with the option of using tibial trays either with or without a male stem. In the event that a tibial tray with a male stem is used, the invention can accommodate a range of sizes of female stems customarily implanted in the intramedullary canal to permit removable implantation of the stem and its associated tibial tray.

Another particularly important feature of the invention resides in the construction of a tibial tray which has only one pair of spaced mounting holes serving a dual purpose. Specifically, each hole individually serves to receive and mount both the cannulated screw for fixedly joining the tibial tray and the wedge and the bone screw for attaching the tibial tray and the wedge, as a unit, to the proximal end of the tibia. Heretofore, it was customary for the tibial tray to be formed with one pair of holes for receiving a fastener from fixedly joining the tibial tray and the wedge and yet another pair of holes for receiving the bone screws for attaching the tibial tray and the wedge as a unit to the tibia. With fewer holes, the tibial tray of the invention thus is stronger than known constructions.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 1 is an exploded view, in perspective, of a modular tibial prosthesis embodying the invention;

FIG. 2 is a top plan view of certain components illustrated in FIG. 1;

FIG. 3 is a cross section view taken generally along line 3—3 in FIG. 2 illustrating one manner of implantation of the prosthesis in a tibia;

FIG. 4 is a detail cross section view in elevation illustrating certain components depicted in FIG. 3 to show various positions which they can assume;

DETAILED DESCRIPTION OF THE PREFERRED EMBODIMENTS

Figure 5A:
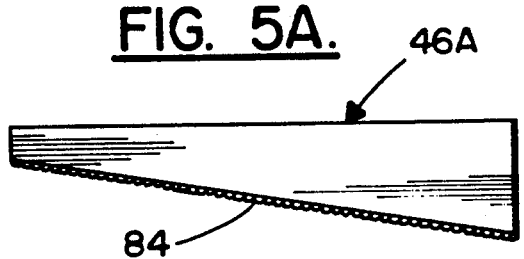
FIGS. 5A, 5B, and 5C are front elevational views, respectively, depicting a prosthetic wedge of the invention with, successively, a medial/lateral slope across its entire surface, a medial/lateral slope in only one compartment, and a medial/lateral slope in only one, but an opposite, compartment.

Turn now to the drawings, and initially, to FIGS. 1–3 which generally illustrate a tibial prosthesis 20 for an artificial knee joint embodying the invention. As seen most clearly in FIG. 1, the tibial prosthesis 20 includes a tibial tray 22 which may be adapted to receive a suitable bearing member (not shown) attachable in any desired fashion to a receiving surface 24.

With continued reference to FIG. 1, the tibial tray 22 is seen to include a tapered male stem 36 and a support shelf 38 of which the receiving surface 29 is a proximal surface. The stem 36 is integrally joined to the support shelf and extends distally therefrom. The support shelf 38 has a somewhat heart-shaped configuration (FIG. 2) generally conforming to the proximal end of the tibia.

While the material choice for the tibial tray 22 and for the other prosthetic components discussed herein may vary, it is important that a relatively durable and strong material be used. Preferable materials are titanium, titanium alloy, or cobalt chrome although stainless steel, ceramics, composites, or polyethylene could be employed. It is also important that the material selected be biologically and physiologically inert and that it be properly sterilized and prepared prior to implantation.

In a manner disclosed in greater detail in commonly assigned U.S. Pat. No. 4,834,081 issued May 30, 1989, the prosthesis 20 can be provided with a female stem 39 which is, in effect, an extension member for the male stem 36. The female stem 39 extends between a nose end 40 and an open tail end 42 to allow for insertion of the male stem 36 into a reception region defined by an inner surface 44. The angle of taper of inner surface 44 with respect to a longitudinal axis of the female stem 39 is substantially similar to the angle of taper of an outer surface of the male stem 36. The angular divergence between the outer surface of the male stem 36 and the inner surface 44 may be such that the two components thereby achieve a locking engagement.

Inasmuch as one aspect of the present invention is the interchangeability of the prosthetic components, the shape and size characteristics of the female stem 39 may vary and, indeed, it would be desirable for a family of different sized stems 39 to be available. The selection of a particular stem length and particular tibial tray configuration is to be governed by the size, shape, and anatomy of the particular patient as well as the nature and extent of the damaged or diseased bones.

Of course, it will be appreciated that neither the male stem 36, nor the female stem 39 are absolutely necessary to the prosthesis 20 and may be totally eliminated, should that be desired.

A primary feature of the invention is the provision of a tibial wedge 46 and of cannulated fasteners 48 and bone screws 50 associated with the wedge. With continuing reference to FIGS. 1-3, the wedge 46 has a proximal surface 52 and a distal mounting surface 54 engageable with the proximal end 56 of a tibia 58 (FIG. 3). The tibial tray 22 has at least a pair of laterally spaced clearance bores therethrough extending between the proximal bearing or receiving surface 29 and a distal surface 62 (FIG. 3). Each clearance bore 60 also has a coaxial counterbore 64 communicating with the receiving surface 24.

Additionally, the wedge 46 has a pair of laterally spaced threaded bores 66 which extend therethrough and are generally aligned with the clearance bores 60 of the platform 38 when the wedge 46 and the tibial tray 22 are joined together in the manner illustrated in FIG. 3. The cannulated fasteners 48 extend through the clearance bores 60 for purposes of fixedly fastening the wedge and the tibial tray as a unit. Each cannulated fastener 48 has a head member 68 and a threaded shank 70 extending from the head member. Each head member 68 is receivable in an associated one of the counterbores 64 and the shank 70 is threadedly engaged with its associated threaded bore 66 in the wedge 46. Diametrically opposed slots 71 are provided in the head member 68 of each cannulated fastener 48 for reception therein of a tool for attachment and removal of the cannulated fastener to and from the tibial tray 22 and the wedge 46.

When the cannulated fastener 48 is completely tightened, the head member 68 is flush with the receiving surface 24 of the platform 38. When this occurs, the proximal surface 52 is matingly engaged with the distal surface 62 as clearly seen in FIG. 3.

Returning to FIG. 1, the wedge 46 is seen to include a centrally positioned aperture 72 extending therethrough between the surfaces 52 and 54 for freely receiving the male stem 36. Furthermore, the wedge 46 is preferably formed with an aperture 72 which is sufficiently large to freely receive the male stem 36 and stem extension 39, each having any size which might be appropriately utilized.

With the wedge 46 and tibial tray 22 joined together in the manner previously described, the unit thereby achieved is placed on the proximal end 56 of the tibia 58 (FIG. 3). The bone screws 50 are then applied to complete the implantation procedure. Each bone screw 50 includes a head member 74 and a threaded shank 76 for threaded engagement with the tibia 58.

Turn now to FIG. 4 wherein the relationship between the bone screw 50 and the cannulated fastener 48 is illustrated in detail. In a first instance, each cannulated fastener 48 has a longitudinal bore 78 which extends through the head member 68 and through the threaded shank 70. It is further formed with a spherical concave surface 80 which communicates with the longitudinal bore 78 in the region adjacent the head member 68. At the same time, the head member 74 of the bone screw 50 is formed with a spherical convex surface 82 adjacent the threaded shank 76 for pivotable slidable engagement with the spherical concave surface 80. As illustrated in FIG. 1, the head member 74 of the bone screw 50 is provided with a tool receiving recess 83 for its attachment to, and removal from the tibia. By reason of this construction, as can be seen in FIG. 4, the bone screw 50 can assume a range of orientations relative to the cannulated fastener 48 while still achieving maximized strength of the resulting implant.

Figure 5B:
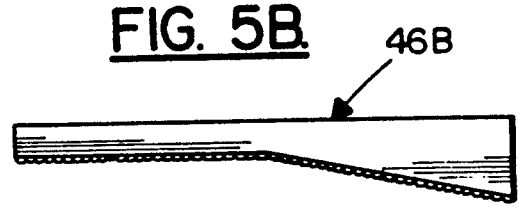
Figure 5C:
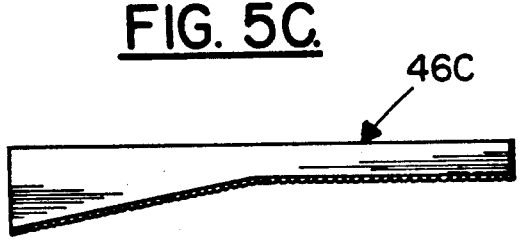
Figure 6:
FIG. 6 is a side elevation view of a tibial wedge of the invention illustrating an anterior/posterior slope.

The tibial wedge 46 which has just been described may be of a variety of shapes and sizes. As to shape, its outer contour would generally be consistent with that of the tibial tray 22. However, as seen in elevation (see FIGS. 5A, 5B, 5C, and FIG. 6) it may be sloped in different ways as well as having different wedge angles. Specifically, as seen in FIG. 5A, a tibial wedge 46A is indicated with a medial/lateral slope across its entire surface; in FIG. 5B, a wedge 46B is indicated which has a medial/lateral slope in only one compartment; and in FIG. 5C, a wedge 46C is indicated with a medial/lateral slope in only one, but an opposite, compartment. In FIG. 6, a tibial wedge 46D is indicated which has an anterior/posterior slope. In each instance, a porous coating 84 may be provide to promote bone ingrowth following implantation.

Figure 7:
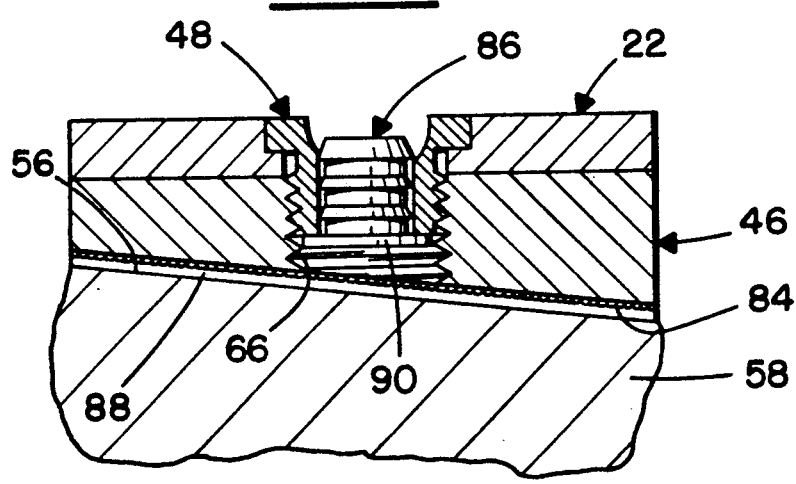
FIG. 7 is a detail side elevation view, in section, of a tibial wedge system of the invention implanted with the use of bone cement, the system utilizing a cement plug.
Figure 8:
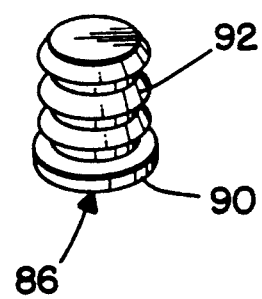
FIG. 8 is a perspective view depicting the cement plug illustrated in FIG. 7.

It was previously mentioned that there is considerable diversity among surgeons as regards the mode of implantation of a prosthesis. Thus, while the construction just disclosed would satisfy the requirements of those surgeons comfortable with bone screws, there are others who rely solely upon bone cement as the fixation medium. The tibial prosthesis 20 will accommodate such an alternative mode. In this instance, viewing FIGS. 7 and 8, a bone plug 86 is used to seal the threaded bores 66 in the tibial wedge 46 against undesired flow of bone cement 88 away from the proximal end 56 of the tibia. Each bone plug 86 has a head 90 which engages a distal end of the cannulated fastener 48, the head 90 being slightly smaller in diameter than the threaded bore 66 in the tibial wedge. Furthermore, each bone plug 86, which may be composed of polyethylene or other suitable plastic material, is provided with a successive series of annular flanges 92 which fittingly engage the longitudinal bore 78 of the cannulated fastener 48 and prevent passage therethrough of the bone cement.

The invention will also accommodate those surgeons desiring a combination of bone screws and bone cement. In this instance, the engagement of the convex surface 82 of the bone screw 50 with the convex surface 80 of the cannulated fastener 48 will serve the same purpose as the bone plug 86 and prevent undesired intrusion of bone cement away from the proximal end 56 of the tibia 58.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A prosthetic system for implantation on the proximal end of a tibia comprising:
   tibial tray means including a distal surface and a proximal surface opposite said distal surface and a pair of laterally spaced clearance bores therethrough, each clearance bore having a coaxial counterbore communicating with said proximal surface;
   wedge means including:
   a proximal surface intimately received on said distal surface of said tibial tray; and
   a distal mounting surface engageable with the proximal end of the tibia and having a pair of laterally spaced threaded bores therethrough generally aligned with the clearance bores, respectively, in said tibial tray means; and
   joinder means for fixedly mounting said wedge means to said tibial tray means prior to implanting said tibial tray means on the proximal end of the tibia, said joinder means including:
   a pair of cannulated fasteners, each having a head member, a threaded shank extending away from said head member, and a longitudinal bore extending through said head member and through said threaded shank, each of said head members being receivable in an associated one of the counterbore, each of said threaded shanks being threadedly engaged with an associated one of the threaded bores to thereby fixedly attach said wedge means to said tibial tray means; and
   bone screw means extending through the longitudinal bore of each of said cannulated fasteners for fixedly attaching said tibial tray means and said wedge means to the tibia.

2. A prosthetic system for implantation on the proximal end of a tibia comprising:
   tibial tray means including a distal surface and a proximal surface opposite said distal surface and having a pair of spaced clearance holes therein;
   wedge means including:
   a proximal surface intimately received on said distal surface of said tibial tray; and
   a distal mounting surface engageable with the proximal end of the tibia and having a pair of laterally spaced threaded bores therethrough generally aligned with the clearance bores, respectively, in said tibial tray means; and
   fixation means receivable through each of the clearance holes for simultaneously fixedly mounting said wedge means to said tibial tray means and attaching said tibial tray means and said wedge means as a unit to the proximal end of the tibia, said fixation means including:
   a pair of cannulated fasteners, each having a head member, a threaded shank extending away from said head member, and a longitudinal bore extending through said head member and through said threaded shank, each of said head members being receivable in an associated one of the counterbores, each of said threaded shanks being threadedly engaged with an associated one of the threaded bores to thereby fixedly attach said wedge means to said tibial tray means; and
   bone screw means extending through the longitudinal bore of each of said cannulated fasteners for fixedly attaching said tibial tray means and said wedge means to the tibia.

3. A prosthetic system as set forth in claim 1 wherein said
proximal and distal surfaces of said wedge means are planar and angularly disposed relative to each other.

4. A prosthetic system as set forth in claim 3 wherein said distal surface of said wedge means is angularly disposed generally in the anterior/posterior direction to accommodate for a similarly shaped deficiency at the proximal end of the tibia.

5. A prosthetic system as set forth in claim 3 wherein said distal surface of said wedge means is angularly disposed generally in the lateral/medial direction to accommodate a similarly shaped deficiency at the proximal end of the tibia.

6. A prosthetic system as set forth in claim 3 wherein said distal surface of said wedge means has a porous coating thereon to encourage bone ingrowth.

7. A prosthetic system as set forth in claim 3 wherein said distal surface of said wedge means has a first substantially planar face portion generally parallel to said proximal surface thereof and a second substantially planar face portion generally angularly disposed relative to said first surface to accommodate a similarly shaped deficiency of the proximal end of the tibia.

8. A prosthetic system as set forth in claim 3 wherein said tibial tray means includes
   a stem integral with said tibial tray means and extending transversely away from said distal surface for reception in the intramedullary cavity of the tibia; and
   wherein said wedge means has an aperture therethrough extending between said first and second surfaces for freely receiving said stem therethrough.

9. A prosthetic system as set forth in claim 8 wherein said stem has an outer surface uniformly tapered with increased distance away from said tibial tray; and
including:
   a female stem having a nose end and an open tail end and an inner surface uniformly tapered and substantially similar to said outer surface of said stem for locking engagement thereon;

the opening through said wedge means being being sufficiently large to freely receive said female stem therethrough.

10. A prosthetic system as set forth in claim 1 wherein each of said cannulated fasteners has a spherical concave surface communicating with the longitudinal bore adjacent said head member; and wherein said bone screw means includes:
   a head member;
   a threaded shank for threaded engagement with the tibia;
   said head member having a spherical convex surface adjacent said threaded shank for pivotal slidable engagement with said spherical concave surface;
   thereby enabling said bone screw means to assume an optimal orientation relative to the tibia.

11. A prosthetic system as set forth in claim 10 wherein said head member of said joinder means has diametrically opposed slots for reception therein of a tool for attachment and removal of said joinder means to and from said tibial tray means and said wedge means; and wherein said head member of each of said bone screws has a tool receiving recess for its attachment to, and removal from, the tibia.

12. A prosthetic system as set forth in claim 1 wherein each of said cannulated fasteners has a longitudinal bore extending through said head member and through said threaded shank; and including:
   plug means sealingly engageable with the longitudinal bore in each of said cannulated fasteners for preventing flow therethrough of cement when said distal mounting surface of said wedge means is in engagement with the proximal end of the tibia.

* * * * *